United States Patent
Ouriev et al.

(10) Patent No.: US 7,228,728 B2
(45) Date of Patent: Jun. 12, 2007

(54) METHOD FOR DETERMINING RHEOLOGICAL PARAMETERS OF A FLUID

(75) Inventors: Boris Ouriev, Niederuzwil (CH); Erich Josef Windhab, Hemishofen (CH)

(73) Assignee: Buehler AG, Uzwil (CH)

( * ) Notice: Subject to any disclaimer, the term of this patent is extended or adjusted under 35 U.S.C. 154(b) by 25 days.

(21) Appl. No.: 10/514,359

(22) PCT Filed: May 19, 2003

(86) PCT No.: PCT/CH03/00319

§ 371 (c)(1),
(2), (4) Date: Feb. 2, 2005

(87) PCT Pub. No.: WO04/001344

PCT Pub. Date: Dec. 31, 2003

(65) Prior Publication Data

US 2005/0126268 A1 Jun. 16, 2005

(30) Foreign Application Priority Data

Jun. 21, 2002 (DE) ................................ 102 27 918

(51) Int. Cl.
*G01N 11/02* (2006.01)
(52) U.S. Cl. .................... 73/54.41; 73/54.01
(58) Field of Classification Search ............... 73/54.41, 73/861.25, 861.27, 861.28
See application file for complete search history.

(56) References Cited

U.S. PATENT DOCUMENTS 4,862,384 A * 8/1989 Bujard et al. ................. 702/54
5,705,753 A * 1/1998 Hastings et al. .......... 73/861.28
5,835,884 A * 11/1998 Brown ......................... 702/45
6,067,861 A 5/2000 Shekarriz et al.
6,378,357 B1 * 4/2002 Han et al. ................... 73/54.41
6,439,034 B1 * 8/2002 Farone et al. ............... 73/54.24
6,446,494 B2 * 9/2002 Hastings et al. ............ 73/54.41
6,796,189 B1 * 9/2004 Umekage et al. ......... 73/861.27

FOREIGN PATENT DOCUMENTS

WO    WO 0237082    5/2002

OTHER PUBLICATIONS

Ouriev et al., "Rhological Study of concetrated suspensions in pressure-driven shear flow using a novel in-line untrasound Dppler method," Experiments in Fluids, Feb. 2002, vol. 32, No. 2, pp. 204-211.*

* cited by examiner

*Primary Examiner*—Hezron Williams
*Assistant Examiner*—Ryan Christensen
(74) *Attorney, Agent, or Firm*—Jordan and Hamburg LLP (57) ABSTRACT

The inventive method uses the ultrasound Doppler method (UVP) in order to determine a local velocity profile perpendicular to a line for a fluid which flows through said line, carrying suspended or emulsified particles. The wall shear stress of said fluid is measured locally within the range of said local velocity profile. Specific rheological parameters of the flowing fluid thus examined, e.g. viscosity function (shear viscosity), flow limit etc., can be determined from the local velocity profile and the local wall shear stress associated therewith. A suitable model is adapted by iteratively adapting a model-based theoretic velocity profile to a measured velocity profile.

30 Claims, 9 Drawing Sheets

METHOD FOR DETERMINING RHEOLOGICAL PARAMETERS OF A FLUID

BACKGROUND OF THE INVENTION

This invention relates to a method and device for determining the rheological parameters of a flowing fluid, in particular of a suspension or an emulsion.

Similar methods and devices are already known. The ultrasound Doppler method is here used to determine a local velocity profile perpendicular to a line for the fluid that flows through a flow channel and carries suspended or emulsified particles. In addition, the static pressure is measured upstream and downstream from the area of the determined local velocity profile to determine a pressure difference along the direction of flow in the area of the local velocity profile. The velocity profile and the associated pressure difference profile can then be used to determine specific rheological parameters of the examined flowing fluid, e.g., the viscosity function (shear viscosity), yield point, etc.

This combination of ultrasound Doppler method (UVP, ultrasound velocity profiling) and pressure difference determination (PD, pressure difference), referred to by experts as UVP-PD for short, has been described in numerous publications in different variants, always with slight modifications.

The article "Velocity profile measurement by ultrasound Doppler shift method" by Y. Takeda in the International Journal of Heat and Fluid Flow", Vol. 7, No. 4, December 1986, confirms the suitability of the UVP method for determining a one-dimensional velocity profile in tubules or blood vessels only several millimeters in diameter.

The "Rheological Study of Non-Newtonian Fluids" by E. Windhab, B. Ouriev, T. Wagner and M. Drost, 1.sup.st International Symposium on Ultrasonic Doppler Methods for Fluid Mechanics and Fluid Engineering, September 1996 describes the aforementioned UWP-PD method.

"Ultrasound Doppler Based In-Line Rheometry of Highly Concentrated Suspensions" by B. Ouriev, Diss. ETH No. 13523, Zurich 2000, contains an extensive description of the theoretical and equipment-related principles of the UVP-PD method along with its application in drag shear flows and pressure shear flows, in particular of model suspensions or given rheological fluids, e.g., during the manufacture of chocolate or pasta products. This publication deals with both laminar and turbulent flows.

The UVP-PD method described here yields good results for different kinds of velocity profiles and for the rheological parameters to be determined for the examined fluids. However, the two spaced apart measuring points are always required for measuring the pressure upstream and downstream from the determined velocity profile. While use can today be made of slightly intrusive miniaturized ultrasound transceivers, ultrasound measuring transducers and pressure sensors, the distance between the two pressure measuring points always required upstream and downstream from the acquired local velocity profile for reasons of measuring accuracy already places limits on a further "compacting" of the UVP-PD measuring device by edging the two pressure sensors together.

BRIEF SUMMARY OF THE INVENTION

An object of the invention is to provide a method and measuring device that uses the ultrasound Doppler method and enables a more compact measuring device along with a simplification of the method complexity relative to the UVP-PD method of prior art.

The method according to the invention for determining the rheological parameters of a flowing fluid, in particular of a suspension or emulsion, requires that the fluid flow be limited at least in some areas by a wall contacting the fluid, and involves the following steps:
  a) Sending into the fluid flow an ultrasound signal transmitted from an ultrasound transmitter at least at one prescribed first frequency f1 at an angle θ, which is different from 90°, relative to the direction of flow;
  b) Receiving into an ultrasound receiver an ultrasound signal reflected by particles entrained in the fluid in respective fluid areas with at least one second frequency f2 that is characteristic for the respective fluid area and shifted relative to the frequency f1 by a respective frequency shift Δf;
  c) Acquiring the local wall shear stress in at least an area of the fluid contacting the wall;
  d) Calculating the at least one frequency shift Δf using the at least one first frequency f1 and the at least one second frequency f2;
  e) Allocating the respective frequency shift Δf to a respective fluid area using the respective running time of the ultrasound signal between the point of transmission from the ultrasound transmitter and point of reception by the ultrasound receiver;
  f) Calculating the fluid velocity of the respective fluid area in which the reflecting particles are entrained using the respective frequency shift;
  g) Calculating rheological parameters of the fluid using the wall shear stress of the fluid acquired in the at least one local wall area and the calculated fluid velocity of the respective local fluid areas of the flowing fluid.

The arrangement according to the invention for determining the rheological parameters of the flowing fluid using the method according to the invention consists of:
  At least one wall area that contacts and borders a fluid flowing in the device at least in partial areas of the fluid interface;
  An ultrasound transmitter for sending an ultrasound signal with at least one preset frequency f1 at an angle θ, which is different from 90°, relative to the direction of flow of a fluid flowing in the device;
  An ultrasound receiver for receiving an ultrasound signal with at least one frequency f2 that can be shifted relative to frequency f1 by a frequency shift Δf;
  At least one shear stress sensor for detecting a wall shear stress in at least one area of the fluid in contact with the wall;
  One computer and processor for calculating frequency differences and allocating a specific frequency difference to a respective fluid area using a respective time difference between the transmission and reception of an ultrasound signal; for calculating the fluid velocity of a respective fluid area using the respective frequency shift; and for calculating rheological parameters of the fluid using the acquired wall shear stress of the fluid and the calculated fluid velocity of the respective fluid areas of the flowing fluid.

The two pressure measurements in prior art are avoided by acquiring the local wall shear stress in step c), i.e., by performing a single shear stress measurement in the area of the boundary layer of the flowing fluid. This makes it possible to reduce the amount of space and cabling required for the measuring arrangement, and also to simplify the method.

Since the method according to the invention requires that the fluid flow be limited at least in partial areas by a wall in contact with the fluid, the method according to the invention can also be applied to fluid flows in a partially open channel, e.g., in a fluid flow driven by gravitational force in an inclined groove, or a fluid flow between the cylinder jacket of the rotor and stator, e.g., in a rotational rheometer. These applications are also facilitated by the compact measuring arrangement for the method according to the invention. It is completely sufficient to examine the behavior of the flowing fluid (fluid velocities in local partial areas) in a local area that accommodates the ultrasound transmitter, the ultrasound receiver or, if necessary, an ultrasound transceiver and the shear stress sensor are located during exposure of the fluid to external influences (shear effect, e.g., owing to pressure differences or inertia forces; drag effect of a fluid that adheres to a moving wall or slides along it with slippage). This makes the method suitable for studying the shear and drag-shear flows, as well as combined shear-drag-shear flows. However, turbulent flows can also be analyzed.

In shear flows, which are kept going by such a wall-shear effect, e.g., in the rotational rheometer of the preceding paragraph, it is even impossible to use the UVP-PD method of prior art, since, while fluid velocities can be determined via UVP, pressure drops along the direction of flow cannot.

By contrast, the method according to the invention in conjunction with the arrangement according to the invention enables the use of UVP both in pure drag-shear flows, mixed driven drag/shear-shear flows, in particular in tubular flows with inner stopper, and naturally in pure shear-shear flows based on the local, in extreme cases even point, measurement of the wall shear stress in the boundary layer area of the fluid. Any experimental "boundary conditions" can hence be selected. This opens up new capabilities for the parameterization of different flows and allocation between such parameters and continuum-mechanical or microscopic, particle-based models.

The transmitted ultrasound signal can be a signal with several discrete first frequencies (f1, f1', f1", . . . ), and the received ultrasound signal can be at least a second signal, each with several discrete second frequencies (f2, f2', f2", . . . ), which are shifted relative to the respective first frequencies (f1, f1', f1", . . . ) by a respective frequency shift $\Delta f$ characteristic for the respective fluid area. This makes it possible to determine the fluid velocity characteristic for a fluid area based on several subtraction operations, for which f2−f1=f2'−f1'=f2"−f1"= . . . =$\Delta f$, at least in first approximation. The arithmetic mean is preferably found for the individual differences to obtain a reliable value for $\Delta f$, and hence for the respective fluid velocity of one of the fluid areas.

The transmitted ultrasound signal can also be a signal with a first frequency spectrum (FS1), and the received ultrasound signal can be at least one second signal with a respective second frequency spectrum (FS2), which is shifted relative to the first frequency spectrum (FS1) by a respective frequency shift $\Delta f$ characteristic for the respective fluid area. Frequency shifts can here also be used at several points in the two frequency spectra for averaging the value $\Delta f$, and hence determining the respective fluid velocity of one of the fluid areas.

Pulsed signals are preferably used for the transmitted, and hence also for the received ultrasound signals. In step e) of the method according to the invention, this simplifies the allocation of the respective frequency shift $\Delta f$ and a respective fluid area using the respective running time of the ultrasound signal between the time it leaves the ultrasound transmitter and is received by the ultrasound receiver. In particular, the pulsed signals here each have a constant carrier frequency.

The transmitted and received ultrasound signals can also each be continuous signals, however. This is advantageous in particular when using the frequency spectra FS1 and FS2 described further above.

The wall shear stress is best acquired only in a single area of the fluid in contact with the wall. This enables a particularly compact realization of the method according to the invention.

The ultrasound signal radiated into the fluid is best transmitted and the reflected ultrasound signal is best received at the same location, e.g., by means of an ultrasound transceiver.

A local velocity profile is preferably established transverse to the direction of flow using the fluid velocities of the fluid areas of the fluid calculated in step f), wherein the viscosity function (shear viscosity) of the fluid is determined in particular from the local velocity profile calculated in step f) and the local wall shear stress acquired in step c) in at least one area of the fluid in contact with the wall.

In the method according to the invention, a suitable model is preferably tailored by iteratively adjusting a model-based theoretic velocity profile to a measured velocity profile. Diverse rheological parameters can then be derived from the adjusted theoretical velocity profile.

The measured velocity profile are preferably processed before the adjustment, wherein the measured velocity profiles are subjected to time averaging in particular. This yields more reliable velocity profiles for the subsequent model adjustment.

A respective statistical fluctuating variable, in particular the standard deviation, is preferably determined from the ascertained wall shear stresses and/or the ascertained velocity profile, and compared with a prescribed limiting value for the fluctuating variable. This comparison is preferably used as the basis for selecting reliable measured data.

A suitable model can be selected by checking the boundary conditions used in the model. For example, it can be assumed that the velocity of the fluid at the wall is zero, i.e., that there is wall adhesion. Depending on whether curve adjustment is successful or not, this assumption can be accepted or rejected. The assumption that the velocity of the fluid at the wall differs from zero can e handled in like manner.

The boundary conditions can also be advantageously checked by counting failed iteration steps during the attempted adjustment of a model, wherein another model with different parameters and/or different boundary conditions is selected in particular when a preset number of iteration steps has been exceeded.

The used models are preferably selected from the following group of models:
Power law model
Herschel-Bulkley model
Cross model
Other rheological models can also be used.

The used boundary conditions are preferably selected from the following group of boundary conditions:
Fluid velocity at the wall is zero, or presence of wall adhesion
Fluid velocity at the wall is not zero, or presence of wall sliding
Yield point dipped below in an area of the fluid flow, or stopper present in flow Yield point not dipped below in any area of the fluid flow, or stopper not present in flow Flow state: laminar Flow state: turbulent The used models and boundary conditions are described in "Ultrasound Doppler Based In-Line Rheometry of Highly Concentrated Suspensions" by B. Ouriev, Diss. ETH No. 13523, Zurich 2000, or in "Rheological study of concentrated suspensions in pressure-driven shear flow using a novel in-line ultrasound Doppler method' by B. Ouriev and E. J. Windhab, Experiments in Fluids 32 (2002).

At least some of the determined rheological parameters of the fluid can also be compared with values for this parameter that were ascertained in other ways. This makes it possible to additionally verify the results for the rheological parameters. The other method for determining the rheological parameters preferably involves measuring the viscosity in a rotational rheometer and/or in a capillary rheometer.

The static fluctuating variable, in particular the standard deviation, is best determined for the acquired velocity signals for each velocity channel (=location in velocity profile) and/or for the acquired pressure signals of each pressure measuring point. This information can be used among other things to tell whether the flowing fluid is in a turbulent or laminar flow state.

The arrangement according to the invention preferably has only one shear stress sensor, which is situated in the at least one wall area, and is used to acquire a wall shear stress in at least one area of the fluid in contact with the wall.

In one embodiment of the arrangement according to the invention that is especially preferred, since it is particularly compact, the shear stress sensor, ultrasound transmitter and ultrasound receiver or ultrasound transceiver are arranged in the at least one wall area.

In another preferred embodiment, the arrangement according to the invention can have at least a first wall area and a second wall area, between which a fluid flowing in the device can respectively stream, and which contact and limit the fluid boundary at least in partial areas, wherein an ultrasound transmitter is preferably situated in the first wall area, and an ultrasound receiver in the second wall area. This makes it possible to use ultrasound waves that are not directionally reversed by 180°, but undergo only a relatively small directional change, when reflected/scattered by the particles entrained in the liquid. This ensures approximately the same running time or approximately the same path length in the flowing medium for all ultrasound waves received at the opposing ultrasound sensor. As a result, the traversed, flowing medium exercises approximately the same dampening effect on practically all ultrasound waves reflected/scattered between the ultrasound sensor and ultrasound receiver via particles in various interspersed fluid areas. However, one must remember that, while the absorption of received sound waves evens out as the deviation angle of the sound waves reflected/scattered on the moved particles decreases, this is necessarily accompanied on the one hand by a correspondingly reduced resolution during the localization of the respective reflecting fluid areas in step a) of the method according to the invention, in particular when using pulsed signals, and on the other hand by lower frequency shifts. However, the frequency shifts also increase as the flow velocities rise in the fluid, thereby at least offsetting the impact of the low deviation angle.

A first ultrasound transceiver is preferably situated in the first wall area, and a second ultrasound transceiver in the second wall area. This makes it possible to irradiate the flow with ultrasound waves "from left to right" and simultaneously "from right to left", so that "left" and "right" measuring results can be obtained. This is particularly advantageous when the question is whether the certain asymmetries in the experimentally determined velocity distribution transverse to the direction of flow are only metrological artifacts or actual asymmetries in the real velocity distribution in the fluid. Such artifacts mimic an asymmetry in velocity distribution, and can generally be corrected by averaging the two distributions affected by the artifacts. If the averaged result is then still asymmetrical, this points to an actual asymmetry in the flow.

A first ultrasound transceiver and a first shear stress sensor are preferably situated in the first wall area here as well, while a second ultrasound transceiver and second shear stress sensor are arranged in the second wall area.

The wall area of the arrangement can be the interior wall of a tube or channel section that can be integrated into a line or channel for fluid transport, wherein the ultrasound transceiver and shear stress sensor are preferably integrated in a compact ultrasound transceiver/shear stress sensor measuring transducer unit. The arrangement can additionally incorporate a pressure sensor. This makes it possible to design not only each individual element of the arrangement like a "probe", but the entire arrangement according to the invention, which ensures an even better "process accessibility" of the method according to the invention.

Additional advantages, features and possible applications of the invention can be gleaned from the following description of preferred exemplary embodiments, which are not to be regarded as limiting.

BRIEF DESCRIPTION OF THE DRAWINGS

Accompanying the specification are figures which assist in illustrating the embodiments of the invention, in which.

DETAILED DESCRIPTION OF THE INVENTION

Figure 1:
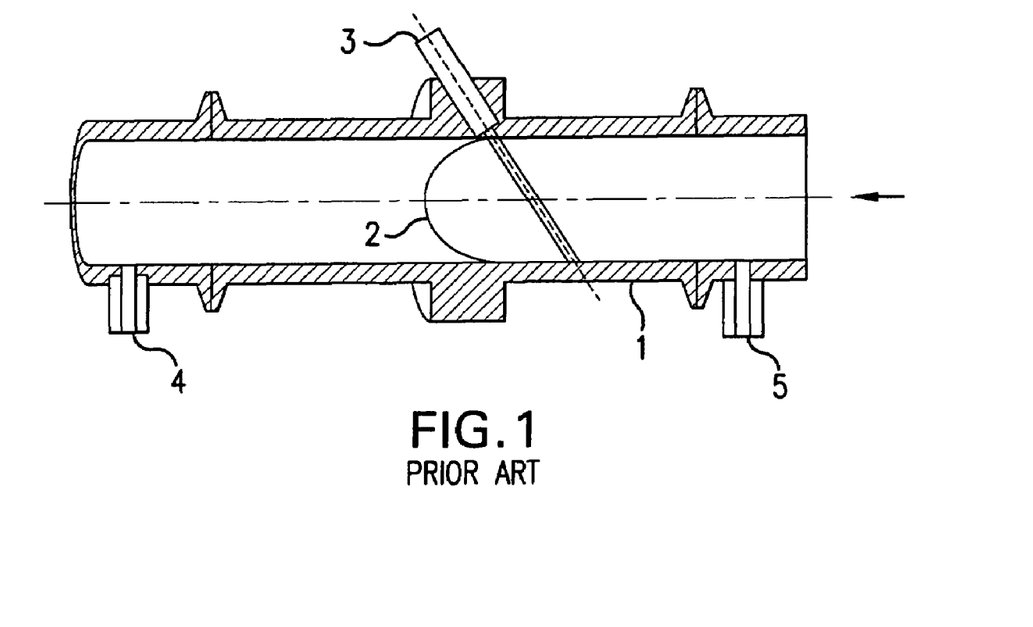
FIG. 1 is a measuring arrangement according to prior art.

FIG. 1 shows a tube section 1 in which a fluid 2 flows. The measuring arrangement on FIG. 1 comprises an ultrasound transceiver 3 as well as a pressure sensor 4 downstream and pressure sensor 5 upstream from the ultrasound transceiver 3.

According to the ultrasound Doppler method (UVP method), an ultrasound transceiver 3 sends out a narrow ultrasound wave US with a frequency f1 (practically flat wave or parallel beam) into the flowing fluid 2 transverse to the direction of fluid flow. The ultrasound wave US is reflected or scattered by moving particles that are entrained in the flowing fluid 2. The portion of the ultrasound wave US reflected or scattered back into the ultrasound transceiver 3 has a shifted frequency f2 owing to the particle motion (Doppler shift). This frequency shift provides information about the velocity of the particles or fluid in a specific fluid volume. The acquired varying frequency shifts are allocated to locations in the fluid where the frequency-shifting reflection or scattering takes place by measuring the running time between when the ultrasound wave was transmitted and received at the ultrasound transceiver 3. This is why pulsed ultrasound waves are used. The smaller the distances between the sequentially received reflected ultrasound pulses are in terms of time, and hence location, the greater the local resolution and number of acquired frequency shifts. The velocity profile can be determined in this manner.

The two pressure sensors 4 and 5 are used to measure a first static pressure P1 downstream and a second static pressure P2 upstream from the area of the fluid flow traversed by the ultrasound waves. The wall shear stress in the fluid is then determined from this.

The viscosity function (shear viscosity) of the fluid can be determined by combining the fluid velocity distribution ("reaction of the fluid") transverse to the direction of flow and the fluid wall shear stress ("external influence on the fluid").

In addition to determining the fluid-wall shear stress and the fluid velocity profile, a suitable model for the viscosity function (shear viscosity) along with suitable boundary conditions for the flowing fluid are selected according to the invention.

Figure 2:
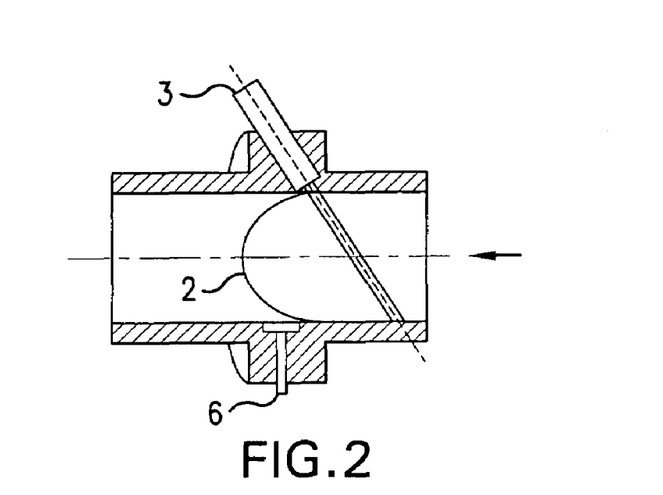
FIG. 2 is a measuring arrangement according to the invention.

FIG. 2 also shows a tube section 1 in which fluid 2 flows. The measuring arrangement on FIG. 2 comprises an ultrasound transceiver 3 as well as a shear stress sensor 6 opposite the ultrasound transceiver 3 in the area in which the velocity profile is to be acquired.

According to the ultrasound Doppler method (UVP method), the ultrasound transceiver 3 is used to determine the velocity profile as already described on FIG. 1 here as well.

However, a shear stress sensor 6 that enables a local determination of wall shear stress in the fluid is here used instead of the two pressure sensors 4 and 5. The wall shear stress is here determined directly and in the area where the velocity profile is also determined via UVP. While a "global", indirect acquisition takes place in prior art (FIG. 2), in which the entire distance between the two pressure sensors is necessarily averaged, the arrangement according to the invention is used in the inventive method to rather perform a "local", direct determination of the wall shear stress. Therefore, an allocation between the actual values for the wall shear stress (boundary condition) at the location of the acquired velocity profile and the velocity profile belonging to this boundary condition ends up taking place.

The fluid velocity distribution ("reaction of the fluid") transverse to the direction of flow and the fluid wall shear stress ("external influence on the fluid") can here again be combined to determine the viscosity function (shear viscosity).

Figure 3:
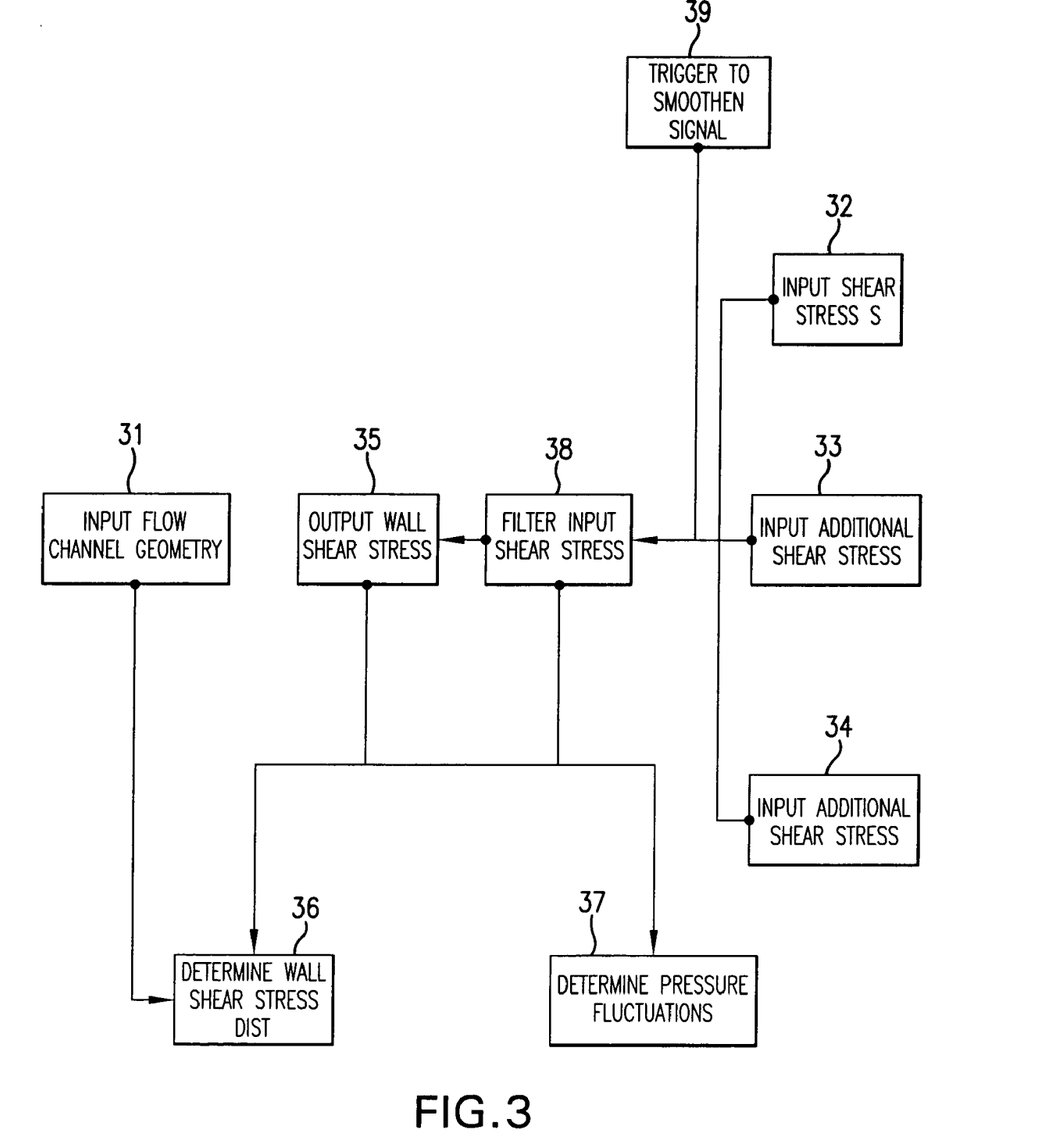
FIGS. 3 to 7 in diagrammatic fashion is the procedure according to the invention for processing and evaluating the measured values acquired with the measuring arrangement in FIG. 1.

FIG. 3 diagrammatically shows the process for evaluating the measured shear stress information to determine the wall shear stress in the fluid. The geometry of the flow channel is input at 31. The shear stress S is input at 32, while additional shear stresses are input as needed at 33 and 34. Up to N different shear stresses S1 to SN can (optionally!) be input. The input shear stress value is filtered in a filter at 38 via a triggering that takes place at 39 in order to smooth out the signal. A wall shear stress is then output at 35. The wall shear stress distribution is determined at 36, and pressure fluctuations as a rule measured only at one location are determined at 37 as needed.

Figure 4:
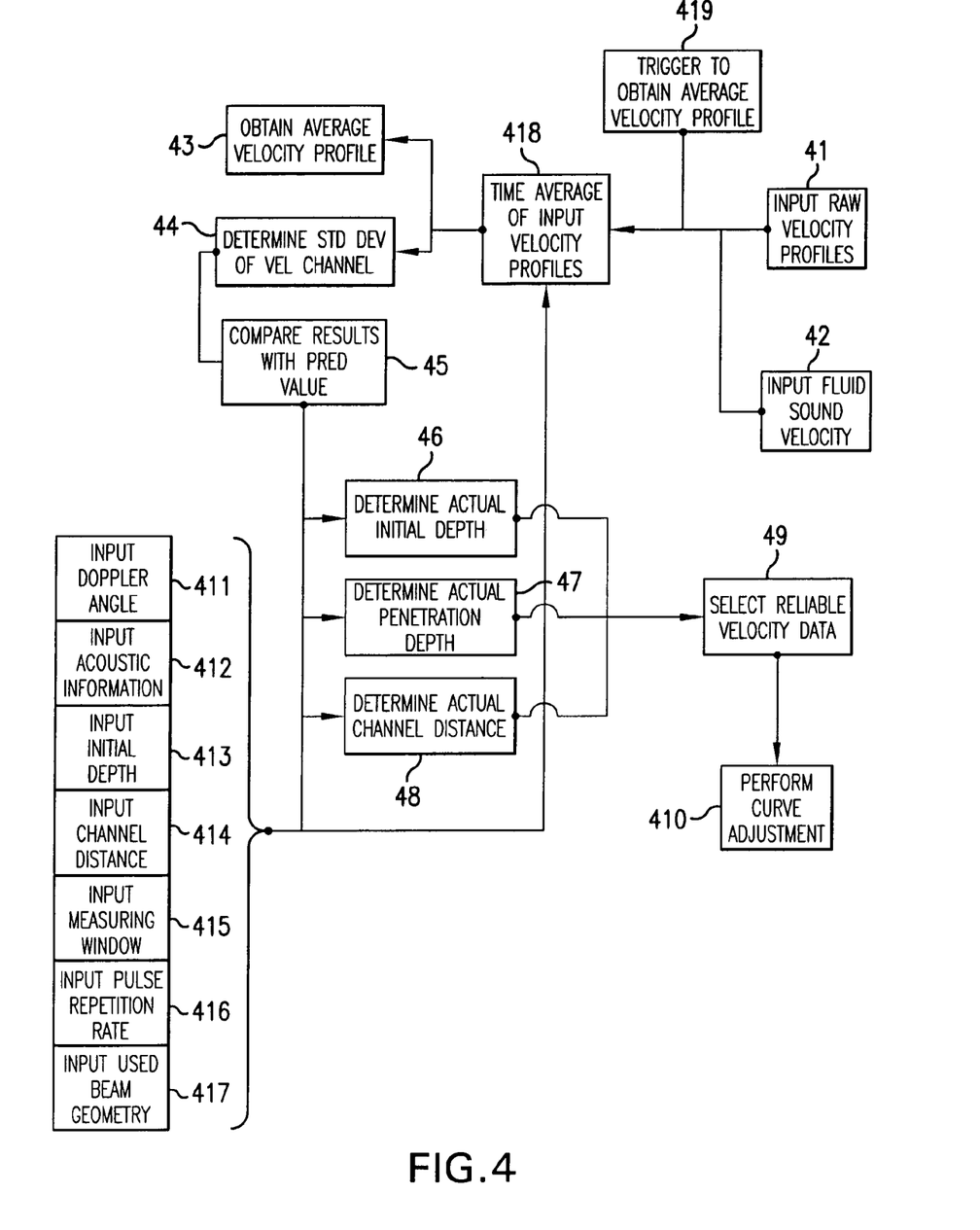

FIG. 4 diagrammatically shows the process for handling the unprocessed, "raw" velocity profiles before curve adjustment. Measured, unprocessed velocity profiles are input at 41. The fluid sound velocity measured for the examined fluid and prescribed sound frequency is input at 42. The values for the input velocity profiles are subjected to time averaging at 418 via a triggering that takes place at 419 to obtain averaged velocity profiles at 43. In addition, the parameters used for the ultrasound Doppler method are input at 418, specifically the Doppler angle at 411, acoustic information at 412, the initial depth at 413, the channel distance at 414, the measuring window at 415, the pulse repetition rate at 416 and the used beam geometry at 417. The standard deviation for each velocity channel of the velocity profile is determined at 44, and then compared with a predetermined limiting value at 45. The actual initial depth, the actual penetration depth and the actual channel distance are then determined from this at 46, 47 and 48, respectively. Proceeding from these three values, reliable velocity data are then selected at 49 for subsequent calculations, which are finally prepared for the curve adjustment at 410.

Figure 5A:
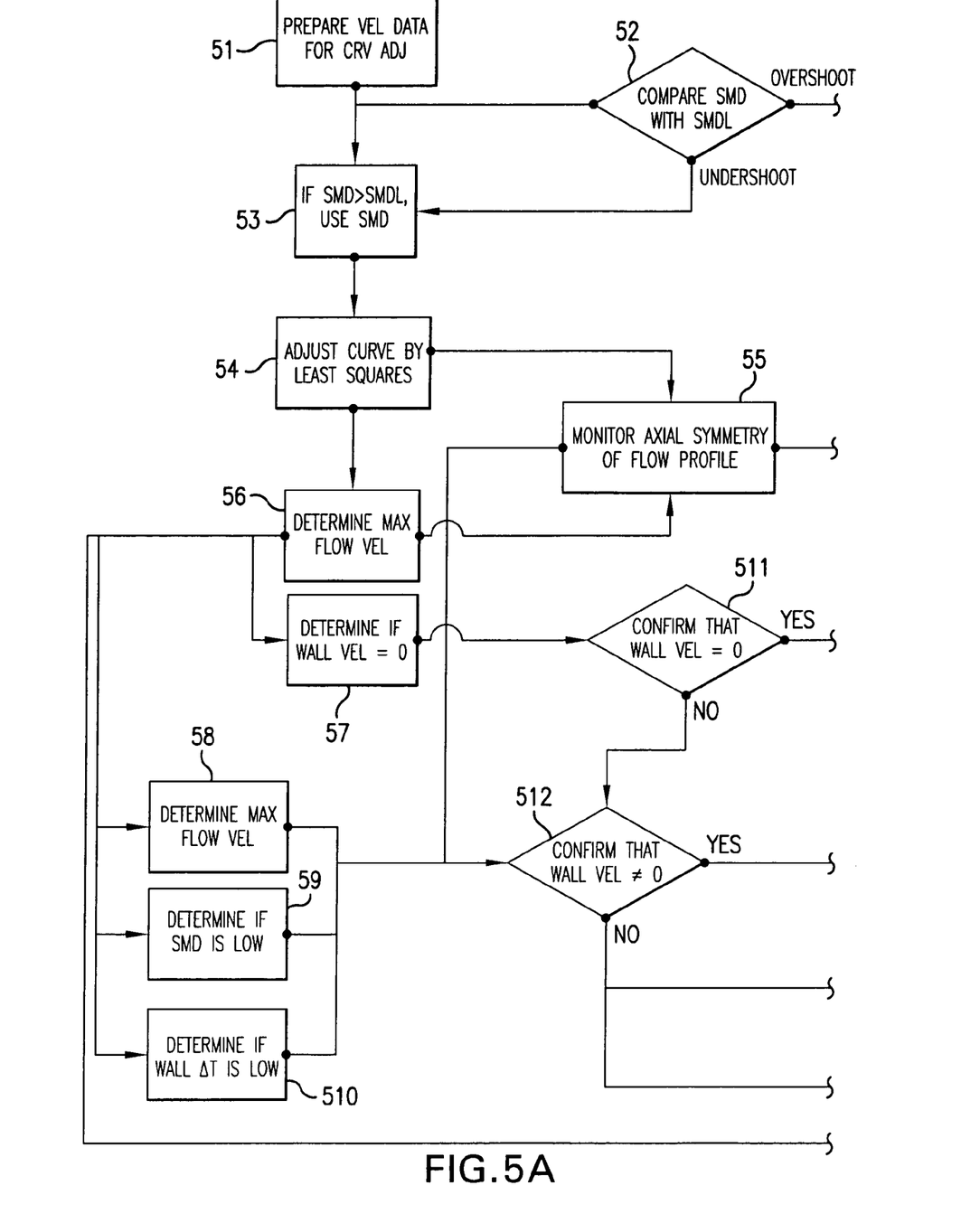
Figure 5B:
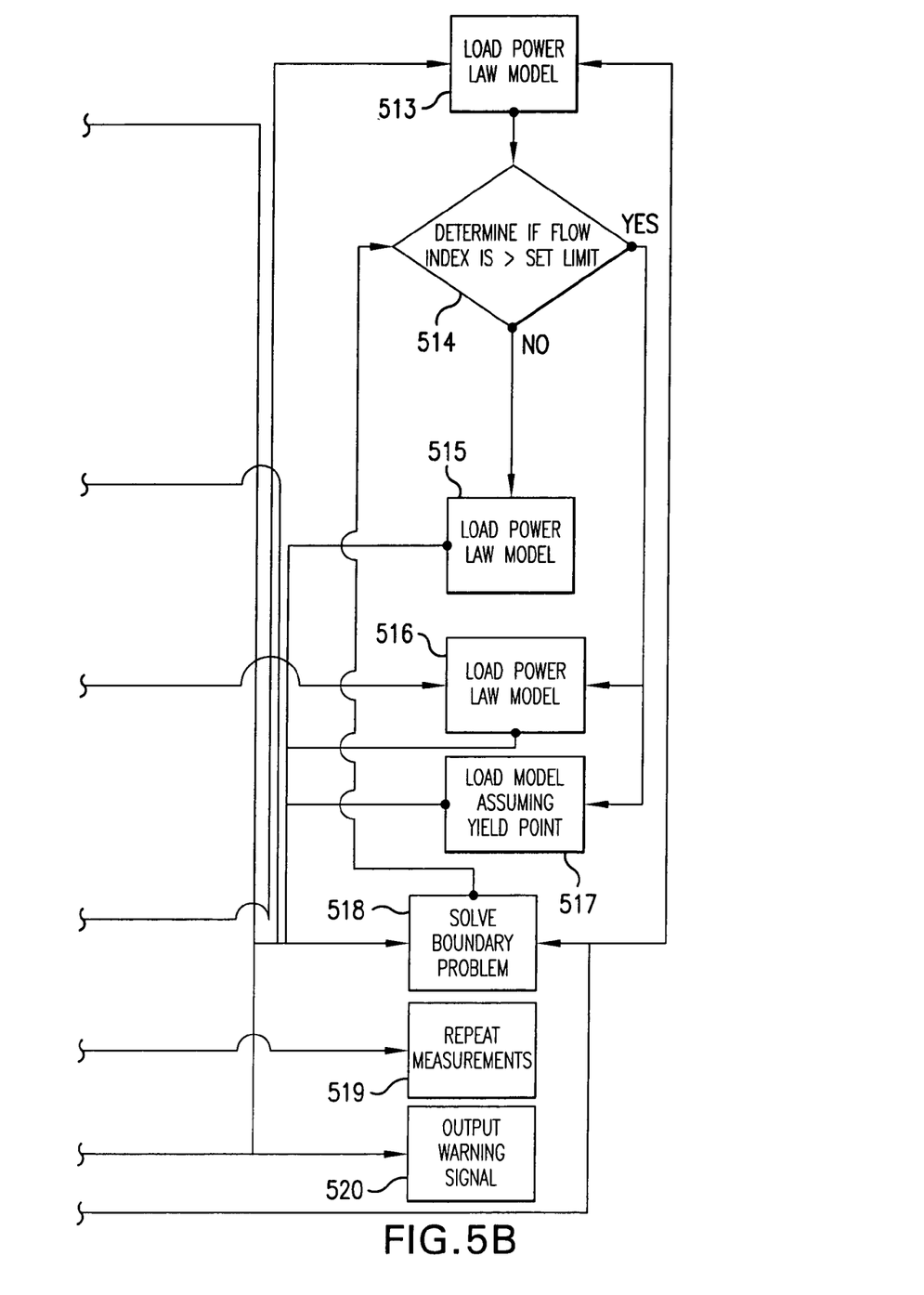

FIGS. 5A and 5B diagrammatically illustrate the process for selecting a suitable model, choosing reliable data and checking the boundary conditions for the flowing fluid. The velocity data for curve adjustment are prepared at 51. The determined standard deviation SMD is compared with a predetermined limiting value SMDL for standard deviation at 52.

If SMD is less than SMDL, a decision is made at 53 to use the SMD to adjust the data (curve adjustment). In this case, a curve adjustment is performed by method of least error squares at 54. This is used at 55 to monitor the axial symmetry of the flow profile, and at 56 to determine the maximum flow velocity. If SMD is greater than SMDL, the process of solving the boundary value problem is initiated at 518, and a warning signal is output at 520. The warning signal indicates that the boundary conditions have not been satisfied.

It is determined whether the wall velocity is zero at 57. If it is then confirmed that the velocity at the wall differs from zero at 511, the power law model is loaded at 516 with the assumption of a wall sliding effect. By contrast, if it is denied at 511 that the velocity at the wall differs from zero, this statement (velocity at the wall is zero) is taken as a condition at 512. It is determined whether the maximum flow velocity is constant at 58, whether the pressure fluctuations are low at 59, i.e., whether the SMD is low, and whether the temperature difference along the flow channel (tube) is low or zero at 510.

If all conditions 58, 59 and 510 are confirmed or satisfied at 512, and if the velocity at the wall is zero, the power law model is loaded at 513 as part of the approach to resolving the problem. If it is then determined at 514 that the flow index is greater than a set limit, the power law model is loaded at 516 with the assumption of a wall sliding effect, and the model assuming a yield point is loaded at 517. By contrast, if it is determined at 514 that the flow index is less than a set value, the power law model is loaded at 515. By contrast, if all conditions 58, 59 and 510 are denied or not satisfied at 512, and if the velocity at the wall differs from zero, the solution involving the power law model is introduced at 518 to determine the flow index, while a repetition of the measurement is initiated at 519, and a warning signal is output at 520.

Figure 6A:
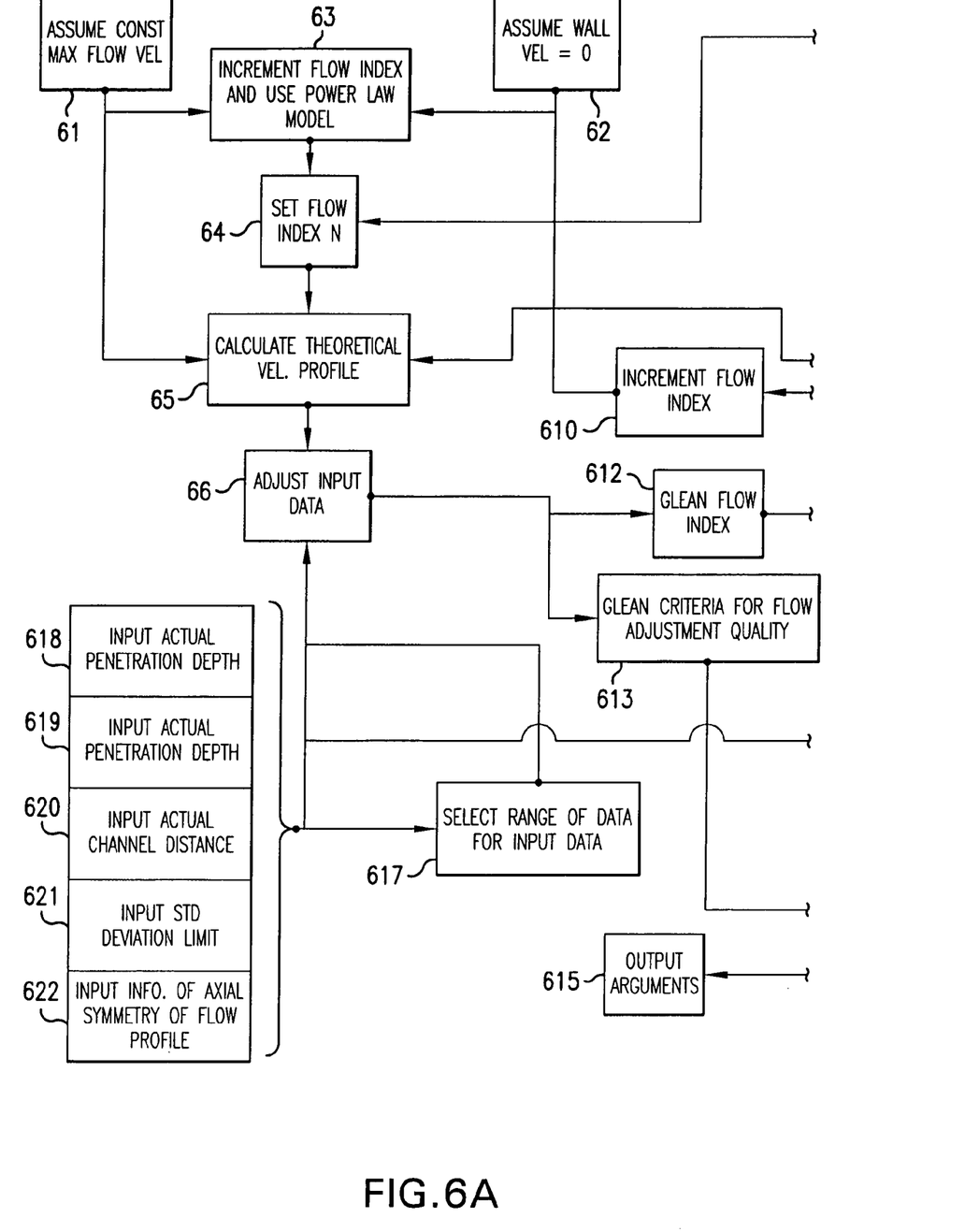
Figure 6B:
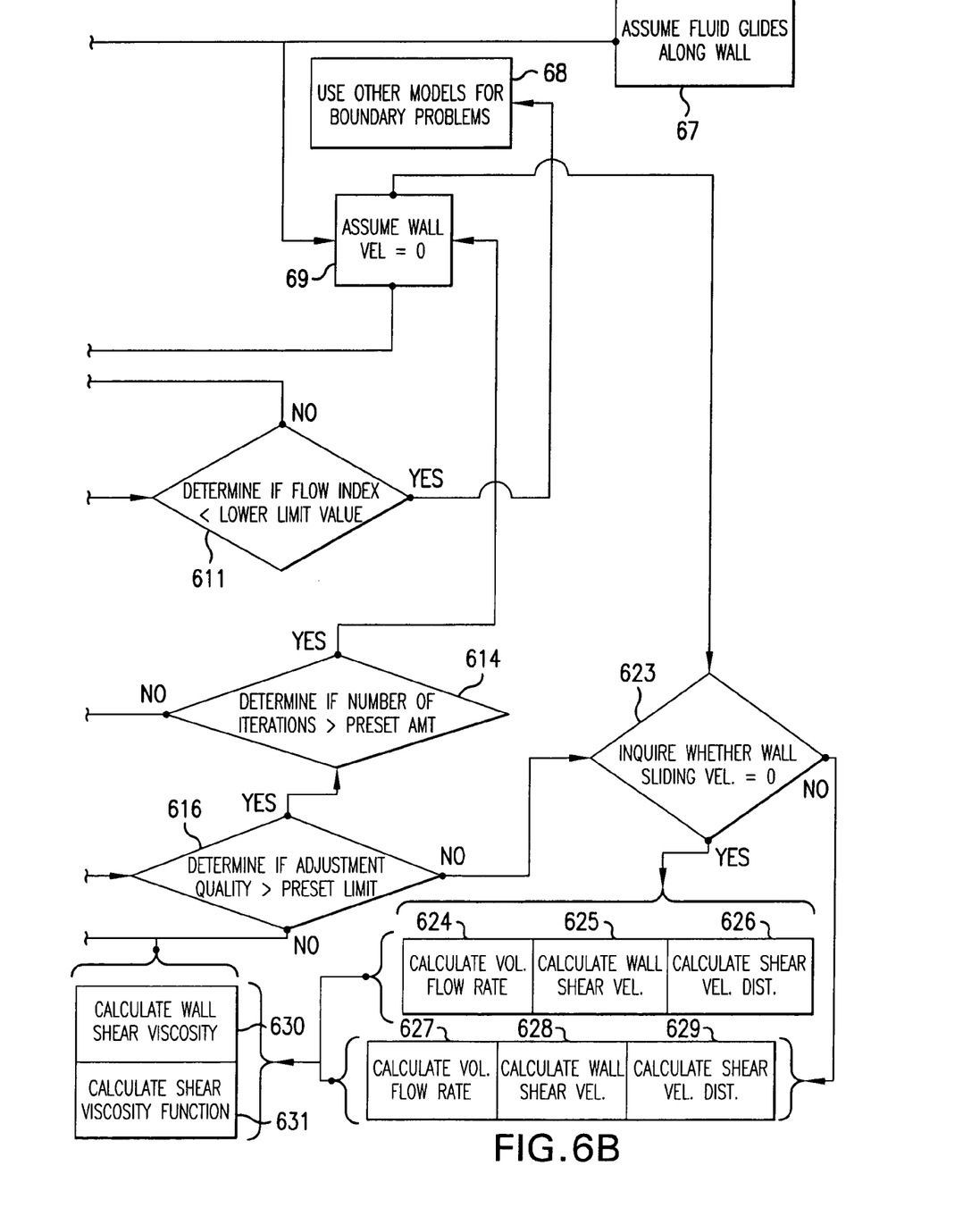

FIGS. 6A and 6B diagrammatically illustrate the process for solving a boundary value problem via curve adjustment, in particular when considering the assumption of wall sliding during curve adjustment.

At 61, it is assumed that the maximum flow velocity is constant. At 62 and in the first iteration of 69, it is assumed that the velocity at the wall is zero. At 63, information from 61 and 62 is used to implement an adjustment using the power law model. The flow index n of the power law model of 67 is then set to n=1 at 64. Under this precondition along with the precondition of 61 and that stemming from 69 to the effect that the sliding velocity on the wall is zero, the theoretical velocity profile is calculated for n=1 at 65.

The input data are then adjusted at 66 by method of least error squares. The data for this purpose are input at 618, 619, 620, 621 and 622, specifically the actual penetration depth at 618, the actual penetration depth at 619, the actual channel distance at 620, the standard deviation exceeding the standard deviation limit at 621, and information about the axial symmetry of the flow profile from the axial symmetry controller at 622. A range of data is selected at 617 from the data input at 618 to 622. The flow index or criteria for adjustment quality are gleaned at 612 and 613 from the adjustment that took place at 66.

It is decided at 611 whether the flow index read at 612 is less than a lowest limiting value or not. If this is not the case, the flow index is incremented at 10), and again used with the power law model at 63. An iterative process is then followed, wherein the steps 610, 63, 64, 65, 66, 612 and 613 are run through repeatedly. If the other case is still present at 611, specifically if the flow index is less than a lowest limiting value, the boundary value problem is resolved using other models at 68.

It is assumed at 67 that the fluid glides along the wall, meaning that the fluid velocity at the wall differs from zero. This assumption is used in conjunction with the power law model at 64 to in turn calculate a corresponding theoretical profile at 65. The process for iteration then continues just as in the preceding paragraph.

It is decided at 616 whether the criteria for adjustment quality read at 613 exceed preset limiting values or not. If this is the case, an inquiry is made at 614 as to whether the number of iterations exceeds a preset number or not. If this is the case, the sliding velocity at the wall is set to zero at 69 in a first iteration step, and iteration is repeated at 65. Otherwise, the iteration is continued. The process for iteration then continues just as in the preceding paragraphs. If it is decided at 616 that the adjustment criteria do not exceed the preset limiting values, the arguments (e.g., flow index, sliding velocity, radius of stopper, etc.) are output at 615, and one continues on to 623.

An inquiry is made at 623 whether the sliding velocity at the wall is zero or not. If it is zero, the volumetric flow rate, wall shear velocity and shear velocity distribution are calculated at 624, 625 and 626 form the adjustment to the velocity profile. If the sliding velocity at the wall is not zero, the respective volumetric flow velocity, wall shear velocity and shear velocity distribution are calculated in an analogous manner at 627, 628 and 629 from the adjustment to the velocity profile assuming wall sliding. Based on the variables calculated at 624 to 626 or at 627 to 629, the wall shear viscosity is then calculated at 630, and the shear viscosity function at 631 (e.g., its distribution along a direction transverse to the flow).

Figure 7A:
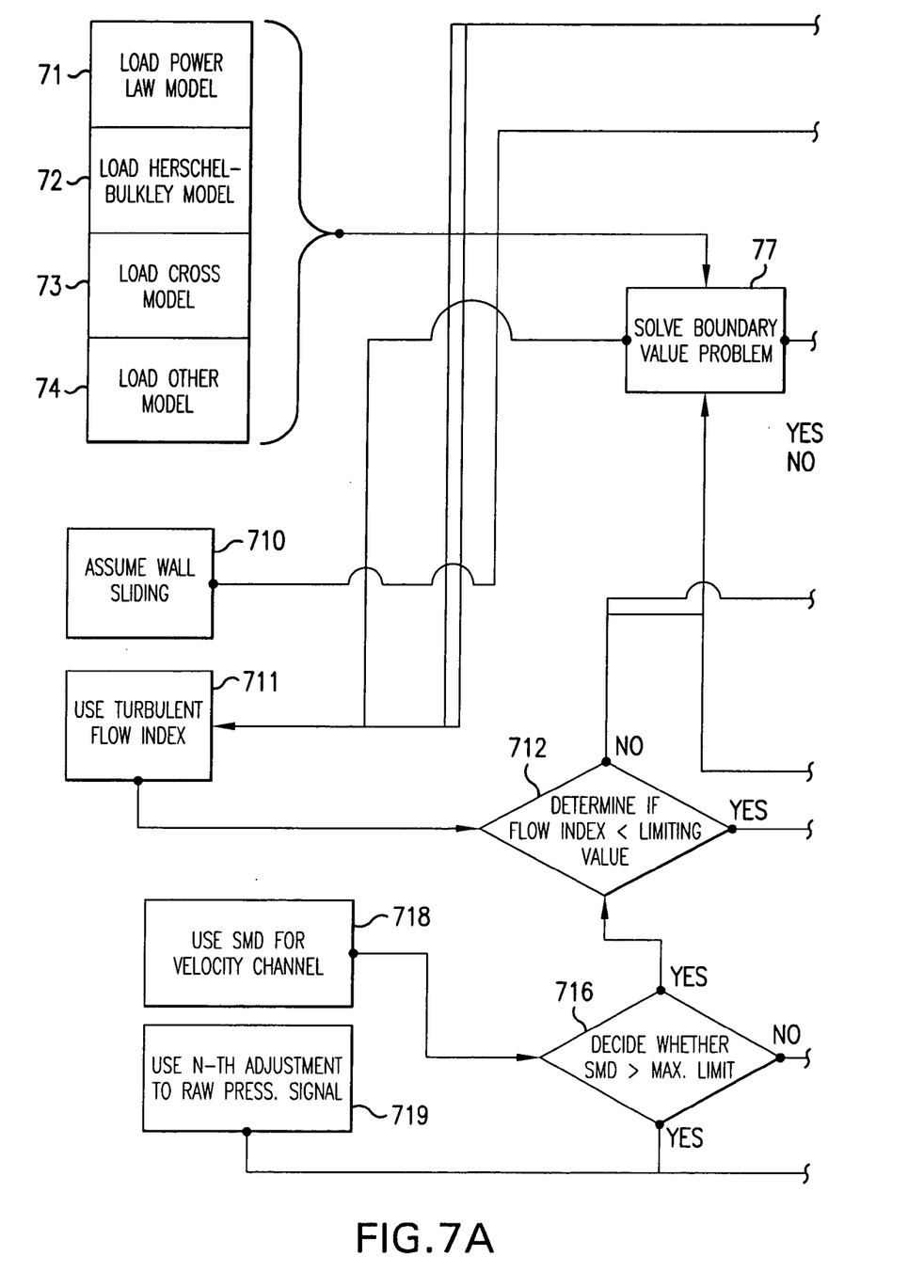
Figure 7B:
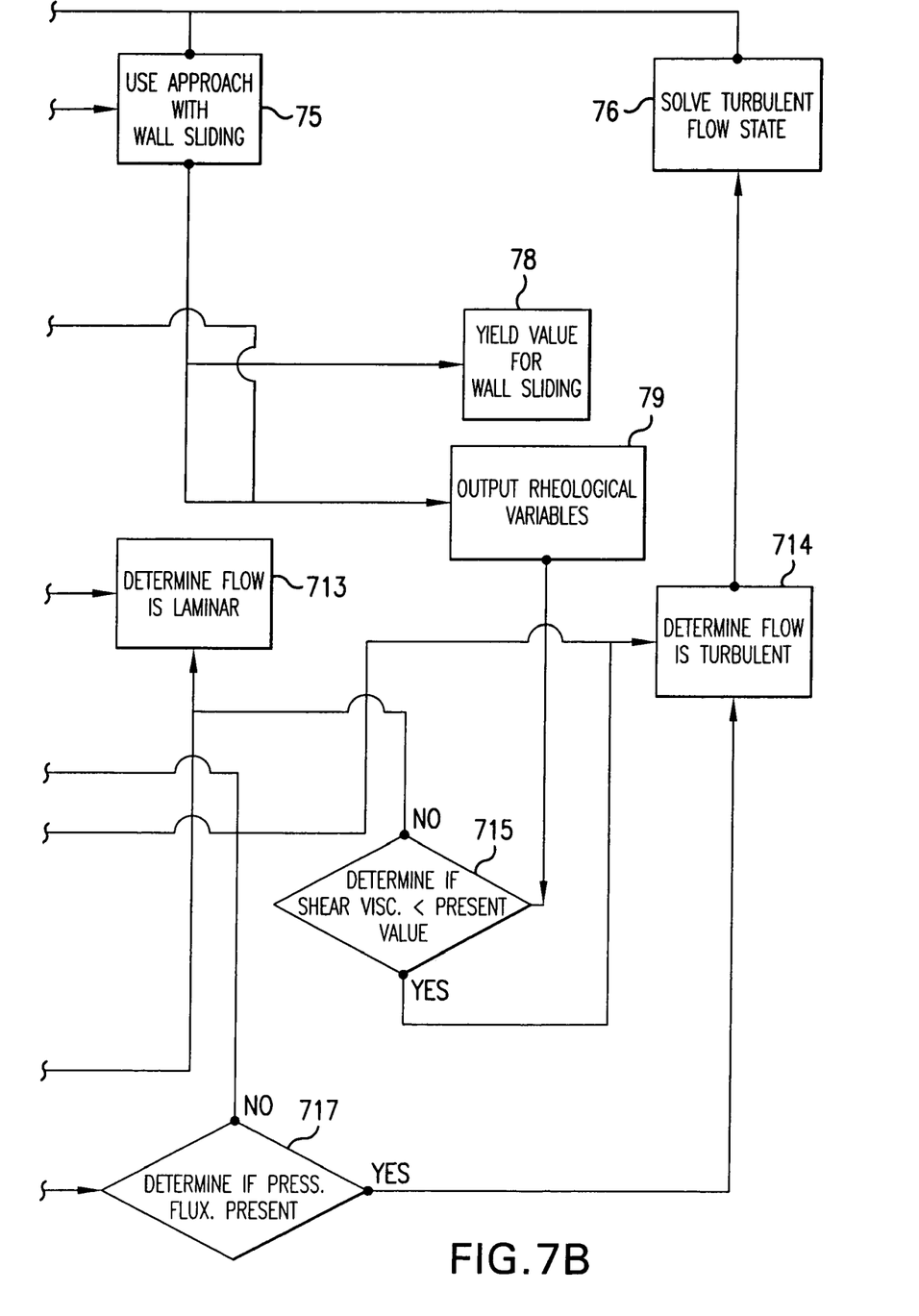

FIGS. 7A and 7B diagrammatically illustrate the process for determining the flow state. The power law model, Herschel-Bulkley model, Cross model or other models are used as the basis at 71, 72, 73 and 74, respectively. The boundary value problem is again solved from this at 77, and the rheological variables are output at 79.

It is decided at 715 whether the shear viscosity calculated from the shear viscosity distribution is less than a preset viscosity limit input by the user, which was used via off-line and/or on-line reference measurements, e.g., utilizing a rotational rheometer, a capillary rheometer or some other rheometer. If the shear viscosity is less than the limiting value, it is decided that a turbulent flow state per 714 is present. If the shear viscosity is greater than or equal to the limiting value, it is decided that a laminar flow according to 713 is present.

An approach to solving the turbulent flow state is used at 76. This approach differs from that used for the laminar flow state only by the adjustment model, which has a similar form, but uses other values for the parameters, e.g., for the flow index. The "turbulent" flow index is then calculated at 76 and used at 711.

It is decided at 712 whether the flow index is less than a lowest limiting value or not. If the flow index is lower, it is decided that a turbulent flow state according to 714 is present. If the flow index is equal to or greater than the lowest limiting value, and based upon an evaluation of the variables for SMD, viscosity, flow index and maximum velocity, it is decided that a laminar flow state according to 713 or a turbulent flow state according to 714 is present, and the approach for the turbulent flow is used at 76.

It is assumed at 710 that wall sliding is present. The approach taking into account wall sliding is used at 75. This yields a value for wall sliding at 78 along with other rheological parameters at 79.

The standard deviation SMD is used as the basis for each velocity channel at 718. It is decided at 716 whether the SMD exceeds a maximum limit or not. If the SMD does exceed this maximum limit, it is in turn decided at 712 whether the flow index is less than the lowest limiting value or not. If yes, the turbulent state according to 714 is present. If no, the laminar flow state according to 713 is present.

The standard deviation SMD of the current n-th adjustment to the unprocessed "raw" pressure signal is used as the basis at 719. It is decided at 717 whether pressure fluctuations are present or not. If pressure fluctuations are present and if permitted by an evaluation of viscosity, flow index and maximum velocity, it is decided that a turbulent flow according to 714 is present, and the approach for the turbulent flow is used at 76. If no pressure fluctuations are present, it is decided for the laminar state, and the approach for the laminar state is used at 77.

In sum, it can be stated that flow types can essentially be divided into the following:

laminar flow with stopper (highly viscous material, e.g., highly concentrated suspension)

laminar flow without stopper (both with flow index n>1, i.e., dilatant or shear-thickening material, and with flow index n<1, i.e., structurally viscous or shear-diluting material)

turbulent flow (low-viscous material, e.g., weakly concentrated suspension).

The ("smoothened") global flow profile of the turbulent flow transverse to the tube axis at which the local velocity fluctuations can be filtered out can be described analogously to the high-viscous stopper flow by the Herschel-Bulkley model, for example.

The present invention may be embodied in other specific forms without departing from its spirit or essential characteristics. The described embodiments are to be considered in all respects only as illustrative and not as restrictive. The scope of the invention is, therefore, indicated by the appended claims and their combination in whole or in part rather than by the foregoing description. All changes that come within the meaning and range of equivalency of the claims are to be embraced within their scope.

The invention claimed is:

1. A device for determining the rheological parameters of a flowing fluid, wherein the device comprises:
- at least one wall area that contacts and borders a fluid flowing in the device at least in partial areas of the fluid interface;
- an ultrasound transmitter for sending an ultrasound signal with at least one preset frequency f1 at an angle θ relative to the direction of flow of a fluid flowing in the device, said angle θ being different from 90°;
- an ultrasound receiver for receiving an ultrasound signal with at least one frequency f2 that can be shifted relative to frequency f1 by a frequency shift Δf;
- at least one shear stress sensor for detecting a wall shear stress in at least one area of the fluid in contact with the wall;
- one computer and processor for calculating frequency differences and allocating a specific frequency difference to a respective fluid area using a respective time difference between the transmission and reception of an ultrasound signal; for calculating the fluid velocity of a respective fluid area using the respective frequency shift; and for calculating rheological parameters of the fluid using the acquired wall shear stress of the fluid and the calculated fluid velocity of the respective fluid areas of the flowing fluid.

2. The device according to claim 1, wherein it only has one shear stress sensor arranged in at least one wall area for determining a wall shear stress in at least one area of the fluid in contact with the wall.

3. The device according to claim 1, wherein the ultrasound transmitter and ultrasound receiver are combined into a single ultrasound transceiver.

4. The device according to claim 1, wherein the shear stress sensor, ultrasound transmitter and ultrasound receiver or ultrasound transceiver are arranged in the at least one wall area.

5. The device according to claim 1, wherein it has at least one first wall area and one second wall area, between which a fluid flowing in the device can respectively stream, and which contact and limit the fluid boundary at least in partial areas.

6. The device according to claim 5, wherein an ultrasound transmitter is preferably situated in the first wall area, and an ultrasound receiver in the second wall area.

7. The device according to claim 5, wherein a first ultrasound transceiver is situated in the first wall area, and a second ultrasound transceiver in the second wall area.

8. The device according to claim 1, wherein a first ultrasound transceiver and a first shear stress sensor are situated in the first wall area, while a second ultrasound transceiver and second shear stress sensor are arranged in the second wall area.

9. The device according to claim 1, wherein the wall area is the interior wall of a tube or channel section that can be integrated into a line or channel for fluid transport.

10. The device according to claim 3, wherein the ultrasound transceiver and shear stress sensor are integrated in a compact ultrasound transceiver/shear stress sensor measuring transducer unit.

11. The device according to claim 3, further comprising a pressure sensor.

12. A method for determining the rheological parameters of a flowing fluid, in particular a suspension or emulsion, wherein the fluid flow is limited at least in partial areas by a wall in contact with the fluid, and wherein the method comprises the following steps:

a) sending into the fluid flow an ultrasound signal transmitted from an ultrasound transmitter at least at one prescribed first frequency f1 at an angle θ relative to the direction of flow, said angle θ being different from 90°;
b) receiving into an ultrasound receiver an ultrasound signal reflected by particles entrained in the fluid in respective fluid areas with at least one second frequency f2 that is characteristic for the respective fluid area and shifted relative to the frequency f1 by a respective frequency shift Δf;
c) acquiring the local wall shear stress in at least an area of the fluid contacting the wall;
d) calculating the at least one frequency shift Δf using the at least one first frequency f1 and the at least one second frequency f2;
e) allocating the respective frequency shift Δf to a respective fluid area using the respective running time of the ultrasound signal between the point of transmission from the ultrasound transmitter and point of reception by the ultrasound receiver;
f) calculating the fluid velocity of the respective fluid area in which the reflecting particles are entrained using the respective frequency shift; and
g) calculating theological parameters of the fluid using the wall shear stress of the fluid acquired in the at least one local wall area and the calculated fluid velocity of the respective local fluid areas of the flowing fluids;

said method further comprising the steps of:
- selecting a suitable model by checking the boundary conditions used in the model;
- attempting adjustment of the selected model;
- determining when an iteration step has passed or failed;
- checking the boundary conditions by counting failed iteration steps during the attempted adjustment of the selected model; and
- selecting another model with other parameters and/or other boundary conditions if a preset number of iteration steps has been exceeded.

13. The method according to claim 12, wherein the transmitted ultrasound signal is a signal with several discrete first frequencies (f1, f1', f1'', . . . ), and the received ultrasound signal is at least a second signal, each with several discrete second frequencies (f2, f2', f2'', . . . ), which are shifted relative to the respective first frequencies (f1, f1', f1'', . . . ) by a respective frequency shift Δf characteristic for the respective fluid area.

14. The method according to claim 12, wherein the transmitted ultrasound signal is a signal with a first frequency spectrum (FS1), and the received ultrasound signal is at least one second signal with a respective second frequency spectrum (FS2), which is shifted relative to the first frequency spectrum (FS1) by a respective frequency shift Δf characteristic for the respective fluid area.

15. The method according to claim 12, wherein the transmitted and received ultrasound signals are each pulsed signals.

16. The method according to claim 15, wherein the pulsed signals each have a constant carrier frequency.

17. The method according to claim 12, wherein the transmitted and received ultrasound signals are each continuous signals.

18. The method according to claim 12, wherein the wall shear stress is determined in step c) in only one area of the fluid in contact with the wall.

19. The method according to claim 12, wherein the ultrasound signal radiated into the fluid is transmitted and the reflected ultrasound signal is received at the same location.

20. The method according to claim 12, wherein a local velocity profile transverse to the direction of flow is generated from the fluid velocities of the fluid areas of the fluid calculated in step f).

21. The method according to claim 20, wherein the viscosity function (shear viscosity) of the fluid is determined from the local velocity profile calculated in step f) and the local wall shear stress acquired in step c) in at least one area of the fluid in contact with the wall.

22. The method according to claim 18, wherein a suitable model is adjusted by iteratively adapting a modellable theoretical velocity profile to a measured velocity profile.

23. The method according to claim 22, wherein the measured velocity profiles are processed before the adjustment.

24. The method according to claim 23, wherein processing involves a time averaging of the measured velocity profiles.

25. The method according to claim 12, wherein a respective statistical fluctuating variable is determined from the measured wall shear stresses and/or the ascertained velocity profiles, and compared with a preset limiting value for the fluctuating variable.

26. The method according to claim 25, wherein the comparison is used as the basis for selecting reliable measured data.

27. The method according to claim 12, wherein the models are selected from the following group of models:
Power law model
Herschel-Bulkley model
Cross model.

28. The method according to claim 12, wherein the boundary conditions are selected from the following group of boundary conditions:
fluid velocity at the wall is zero, or presence of wall adhesion
fluid velocity at the wall is not zero, or presence of wall sliding
yield point dipped below in an area of the fluid flow, or stopper present in flow
yield point not dipped below in any area of the fluid flow, or stopper not present in flow
flow state: laminar
flow state: turbulent.

29. The method according to claim 1, wherein the rheological parameters are determined by measuring the viscosity in a rotational and/or capillary rheometer.

30. The method according to claim 25, further comprising measuring local pressure signals, and wherein the statistical fluctuating variable is determined at least for:
the acquired velocity signals for each velocity channel (=location in velocity profile);
the locally measured shear stress signals;
local pressure signals at pressure measuring points.

* * * * *